United States Patent [19]

Russell

[11] Patent Number: 5,066,279
[45] Date of Patent: Nov. 19, 1991

[54] PROTECTIVE SHEATH FOR HYPODERMIC NEEDLES

[76] Inventor: Donald G. Russell, 86 Windsor Rd., Kensington, Conn. 06037

[21] Appl. No.: 532,456

[22] Filed: Jun. 4, 1990

[51] Int. Cl.⁵ ............................................. A61M 5/00
[52] U.S. Cl. .................................... 604/110; 604/192
[58] Field of Search ................ 604/110, 187, 192, 263

[56] References Cited

U.S. PATENT DOCUMENTS

| | | |
|---|---|---|
| 2,847,995 | 8/1954 | Adams . |
| 3,134,380 | 2/1962 | Armao . |
| 3,320,954 | 5/1967 | Cowley ................................ 604/110 |
| 3,712,302 | 1/1973 | Burke et al. ......................... 604/110 |
| 3,893,608 | 7/1975 | Koenig ................................ 604/110 |
| 4,220,151 | 9/1980 | Whitney .............................. 604/110 |
| 4,332,323 | 6/1982 | Reenstierna . |
| 4,610,667 | 9/1986 | Pedicano et al. . |
| 4,725,267 | 2/1988 | Vaillancourt . |
| 4,735,618 | 4/1988 | Hagen . |
| 4,740,204 | 4/1988 | Masters et al. . |
| 4,799,927 | 1/1989 | Davis et al. . |
| 4,804,370 | 2/1989 | Haber et al. . |

Primary Examiner—John D. Yasko
Attorney, Agent, or Firm—McCormick, Paulding & Huber

[57] ABSTRACT

A protective sheath for encasing a hypodermic needle before and after use includes a funnel-shaped guard at one end to guide a needle into the sheath and protect the user's fingers in the process. The sheath is composed of a tubular sleeve having relatively rigid tube sections at each end and a flexible intermediate section. After a hypodermic needle has been used, the needle is inserted into the protective sheath and the sheath with the encased needle is bent to decommission the needle and capture the needle within the sheath for disposal.

17 Claims, 1 Drawing Sheet

U.S. Patent  Nov. 19, 1991  5,066,279
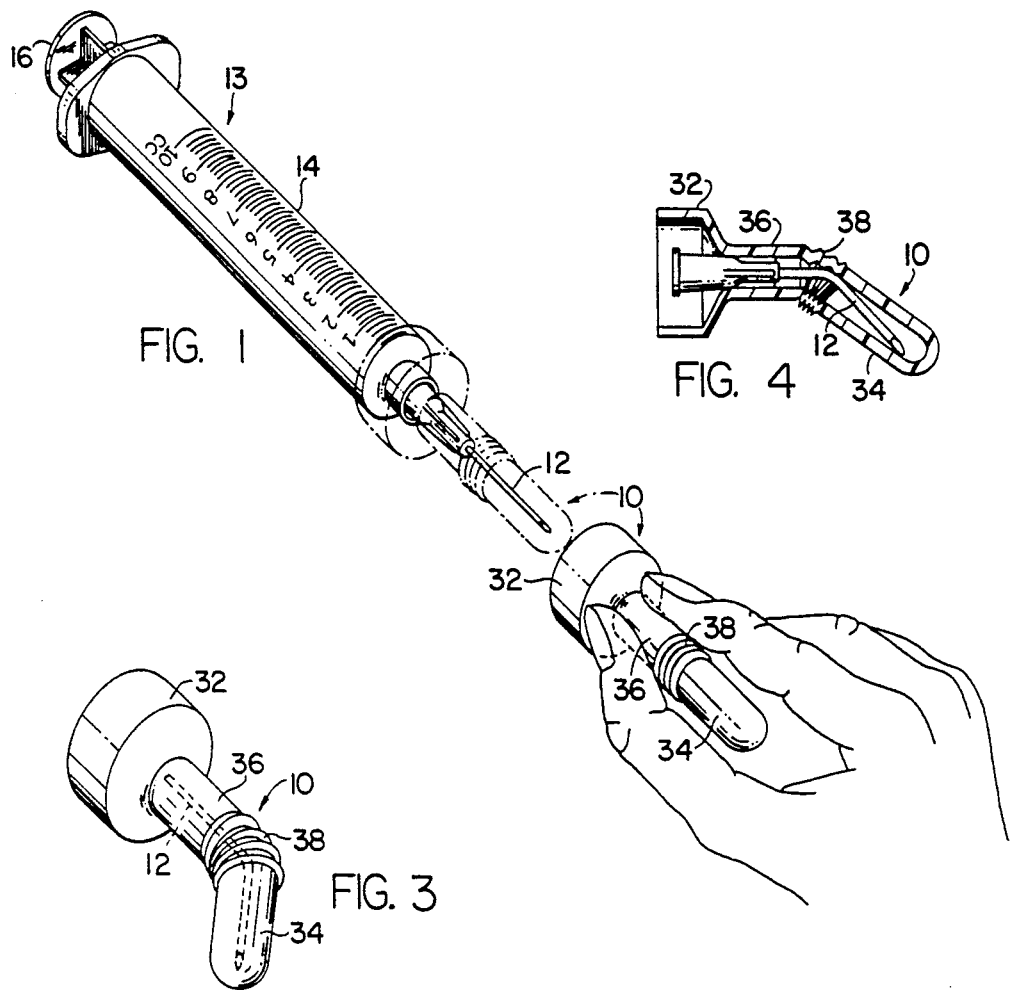

PROTECTIVE SHEATH FOR HYPODERMIC NEEDLES

BACKGROUND OF THE INVENTION

The present invention relates to a protective sheath for use with hypodermic needles before, during and after medical and similar uses. More particularly, the invention relates to a protective sheath that keeps a hypodermic needle sterile prior to use, protects medical personnel while utilizing the needle and serves to decommission and encapsulate the needle after use.

Incidences of injury and the spread of infection and contamination from inadvertent punctures or "sticks" by hypodermic needles are a source of increasing concern in hospitals, physician's offices and other facilities which require medical personnel to handle and dispose of hypodermic needles after they have been used on a patient. Additionally, the appearance of medical waste and particularly "sharps" such as hypodermic needles in areas not approved for disposal or, more importantly, public areas such as beaches and parks where disposal is not permitted, has lead to new environmental regulations governing the disposal of medical waste. The concern for infection of medical personnel and the spread of life-threatening diseases such as viral hepatitis and acquired immunity deficiency syndrome (AIDS) are forcing manufacturers of medical supplies to seek out new forms of protection and disposal to minimize the hazards arising from such waste.

Hypodermic needles pose a special hazard for medical personnel because they are used quite frequently, often in emergency situations where time is critical and care in handling is pre-empted by the exigencies of the situation. Additionally, hypodermic needles are generally supplied with a sheath covering the needle and re-sheathing the needle after use poses a moderate risk of puncture since the sheath has a generally narrow opening and fingers holding the sheath are generally located immediately adjacent the opening. The problem with inadvertent punctures has lead some hospitals to establish regulations that prohibit medical personnel from re-sheathing needles after use. Of course, the consequence of such regulations is exposed, contaminated needles in the medical waste.

Still further problems that arise from hypodermic needles are the pilferage of medical waste by I.V. drug users and the infection that may arise from repeated use of the needles by different users. If the needles were decommissioned after use by authorized facilities, the spread of disease and contamination from pilfered hypodermic needles would be greatly reduced.

The problems discussed above are well known and have been addressed in varying degrees by the prior art. U.S. Pat. Nos. 4,610,667, 4,740,204 and 4,799,927 disclose safety caps or sheaths for enveloping hypodermic needles both before and after use. The caps or sheaths as disclosed in these patents are provided with funnel-shaped mouths or guards which guide the hypodermic needle into the sheath and protect the fingers from inadvertent punctures during the process.

U.S. Pat. Nos. 2,847,995, 3,134,380, 4,725,267 and 4,735,618 disclose hypodermic needles having protective sheaths that cover the hypodermic needle before and after use and collapse during use to permit the injection or extraction of fluids in the body.

U.S. Pat. Nos. 4,332,323 and 4,804,370 both disclose devices for destruction of a hypodermic needle after use. The earlier patent also mentions that a prior art technique for destroying a hypodermic needle includes bending the needle with a protective cap so that the needle can not be again re-used.

It is a general object of the present invention to provide a protective sheath which may be used in conjunction with a hypodermic needle to overcome the problems discussed above.

SUMMARY OF THE INVENTION

The present invention resides in a protective sheath for a hypodermic needle and the method of using that sheath to decommission the needle after use.

The sheath comprises a hollow tubular sleeve having a first longitudinal end with an opening for receiving a hypodermic needle. The tubular sleeve has a second longitudinal end opposite the first, and the length of the sleeve between the two ends is greater than the length of the needle to be encased by the sheath. The tubular sleeve also has a relatively rigid first tube section adjacent the first longitudinal end and a relatively rigid second tube section adjacent the second longitudinal end of the sleeve. An intermediate tube section joining the first and second tube sections is flexible to allow the first and second tube sections to be bent out of axial alignment with one another along with a hypodermic needle that is encased within the sheath. By bending the needle within the case, the needle is crimped and decommissioned which prevents re-use, inadvertent or otherwise, and captures the needle within the sheath for safe disposal. The protective sheath therefore reduces possibilities of injury, infection and transmission of disease.

BRIEF DESCRIPTION OF THE DRAWINGS

FIG. 1 shows a syringe with a disposable hypodermic needle and the technique for encasing the needle with a protective sheath constructed in accordance with the present invention.

FIG. 2 is a side elevation view of the syringe and hypodermic needle of FIG. 1 with the protective sheath installed.

FIG. 3 is a perspective view of the protective sheath encasing the hypodermic needle in a decommissioned condition.

FIG. 4 is a cross-sectional view of the sheath and needle in FIG. 3.

DESCRIPTION OF THE PREFERRED EMBODIMENTS

FIGS. 1 and 2 illustrate the protective sheath 10 of the present invention and its use with a disposable hypodermic needle 12 and an associated syringe 13; however the needle and sheath combination may also be used with I.V. tubing. The syringe is conventional and consists of a plastic cylinder 14 for holding a treatment fluid or body fluid and a plunger 16 for injecting or extracting the fluid. The hypodermic needle 12, usually stainless steel, is a disposable needle and consists of an elongated, hollow needle shaft 20 having a puncture point 22 at one end and an opposite end secured by epoxy or other means in a hub 24. The hub is typically a plastic material and is provided with means such as a flange for securing the needle 12 within the discharge end 18 of the syringe 13. A typical fastening between the hub and the syringe consists of internal threads within the passageway of the syringe end 18 and a compatible flange on the hub 24. Hubs and syringes having such construction are sold by Becton Dickson and Company, Rutherford, N.J. under the trademark LUER-LOK.

FIG. 1 illustrates most clearly the manner in which the protective sheath 10 is employed to maintain sterility of the hypodermic needle 12. The needles and sheath are generally supplied and removed as a unit from a sterile package with the needle installed and held by friction within the sheath so that the sheath provides a protective and sterile cover for the needle. For this purpose and as shown most clearly in FIG. 2, a hermetic seal is established between the hub 24 of the needle and the opening 28 in the elongated tubular sleeve 30 forming the main body of the sheath. A large funnel-shaped mouth or guard 32 adjacent the opening 28 extends over and beyond the exposed end of the hub 24 as shown, for example, in FIG. 4 and prevents fingers and other objects from contaminating the hub after the needle and sheath have been removed from a package.

To install the needle in the syringe for use, the needle 12, while engaged within the protective sheath 12, is inserted into the end 18 of the syringe. The user holds the needle and sheath combination between his fingers while the needle and syringe are twisted to seal the hub 24 in a fluid tight fashion within the end 18 of the syringe. The sheath is then pulled away from the syringe as shown in FIG. 1 to expose the needle 12.

At this point the syringe may be charged with a treatment fluid if an injection is intended or the needle can be inserted into the patient to extract a body fluid. If a delay is anticipated between the time the syringe is charged with a treatment fluid and the actual injection, the protective sheath 10 can be re-installed. Thus, the protective sheath 10 serves the function of protecting the needle against contamination and preserving its sterility at all times.

The protective sheath 10 is comprised basically of the tubular sleeve 30 with the funnel-shaped guard 32 integrally molded from a plastic material such as polyethylene, polypropylene or Nylon. The sleeve 30 has a length greater than the length of the needle so that the needle can be comfortably encased by the sheath when the hub 24 is sealed within the opening 28 of the sleeve 30. At the end of the sheath 10 in which the needle is inserted, the tubular sleeve is enlarged to form the funnel-shaped guard 32 for guiding the hypodermic needle into the sleeve and at the same time protecting the fingers of the user from an inadvertent puncture or "stick". Typically the diameter of the guard would lie between 12 mm to 20 mm. The protective function of the funnel-shaped guard 32 during the insertion of the needle into the sheath is most apparent from the close proximity of the fingers and the needle shown in FIG. 1. The shaped guard not only protects medical personnel using the hypodermic needle from injury but also prevents infection and transmission of disease such a viral hepatitis or AIDS to the medical personnel when the needle 12 is re-inserted into the protective sheath 10 for disposal after use. In an alternative embodiment of the protective sheath 10, the funnel-shaped guard 32 and the tubular sleeve 30 may be dimensioned to allow the guard to extend over and seal against the cylinder 14 of the syringe.

The large guard 32 on the end of the sheath 10 also assists in twisting the needle 12 into and out of engagement with the syringe 13. The large guard serves to enhance the leverage that personnel can apply when securing the needle hub 24 in the syringe 13. The guard insures a tight fit so that there is no leak at the junction. Furthermore, when the hub is securely fastened to the syringe, it prevents inadvertent loosening or disengagement of the needle from the end 18 of the syringe during the course of an injection or injections. Frequently, the syringe and needle are used for multiple injections such as with the administration of a local anesthetic.

Similarly, after the needle 12 has been used, and the needle (still attached to the syringe) is reinserted into the protective sheath 10, the large guard serves again as a lever to permit personnel to easily disengage the needle hub 24 from the syringe 13. Currently, with the needle sheaths of small diameter, it is necessary to grasp the sheath containing the needle with a surgical clamp in order to generate enough leverage to twist the hub from the syringe.

As a further aid to the engagement and disengagement process, a limited degree of lubricant, such as mineral oil, can be added to the end of the hub 24 and the combination of the sheath 10 and needle 12 can be packaged with the lubricant already applied.

In accordance with a further feature of the present invention, the protective sheath 10 is constructed with a tubular sleeve that can be easily bent to decommission the hypodermic needle and encapsulate the needle within the sheath after use. The sleeve 30 as shown most clearly in FIGS. 2, 3 and 4 has relatively rigid tube sections 34 and 36 at each longitudinal end and a bendable intermediate tube section 38 interconnecting tube sections 34 and 36. The sections 34 and 36 are made with wall thicknesses of sufficient thickness to guide the hypodermic needle 12 into the passageway through the sleeve without puncturing the wall and also to allow the sleeve to be grasped and bent to move the sections 34 and 36 from a position in axial alignment as shown in FIGS. 1 and 2 to a bent position out of axial alignment as shown in FIGS. 3 and 4. The bending occurs at the intermediate tube section because of the flexible wall portions. In the illustrated embodiment of the invention, the flexibility is obtained by forming the intermediate section with a plurality of pleats or corrugations extending circumferentially around the sleeve. The pleats allow the walls to fold and unfold without generating stress or fracturing the sleeve.

In the course of bending the sheath 10 with a hypodermic needle encased inside the passageway of the sheath, the needle also assumes a bent position and is thereby crimped and decommissioned so that it cannot be further used by error or intentionally. The bent needle is not only decommissioned but serves as a clear indicator to medical personnel that the needle has already been used and should not be used again.

The operation of the protective sheath to decommission the needle can be performed while the needle is still engaged with the syringe by inserting the hypodermic needle back into the tubular sleeve of the sheath to fully envelope the needle and then bending the sheath and the enveloped needle. Alternatively, the needle can be inserted into the sheath, then be removed from the end of the syringe with the aid of the funnel-shaped guard 32 and then be bent while still inserted within the sheath but disconnected from the syringe. In either event the needle if bent to a sufficient angle remains captured within the tubular sleeve because the sleeve sections cannot be brought into an aligned position that would allow the bent needle to be withdrawn or fall out of the sheath. The sheath in combination with the needle can be disposed of without fear of punctures or "sticks" and without a likelihood of an inadvertent or intentional re-use of the needle.

Thus, the novel protective sheath offers sterility for the needle before the needle is actually used, protects operating personnel and others in the vicinity of the needle from inadvertent punctures before and after use, minimizes the spread of communicable diseases and infection, prevents the needle from being re-used, provides an indication that the needle has been used and discourages pilferage of waste for used needles.

While the present invention has been described in a preferred embodiment, it should be understood that numerous modifications and substitutions can be made without departing from the spirit of the invention. For example, it should be clear that the dimensions of the sleeve and needle can be adjusted for needles for various sizes and lengths. It is desirable that the bendable section of the protective sleeve be located along the needle shaft at a position which bends the needle at a point effectively capturing the needle within the sheath. The end of the protective sheath opposite from the end in which the needle is inserted is preferably closed but may be left open if the sleeve extends well beyond the end of the inserted needle. The frictional engagement between the hub of the needle and the sleeve is established by controlling the dimensions and materials from which the two components are made, but other forms of securing the needle within the sheath can also be provided. Accordingly, the present invention has been described in a preferred embodiment by way of illustration rather than limitation.

I claim:

1. A protective sheath for a hypodermic needle comprising:
    a tubular sleeve having a first longitudinal end with an opening for receiving a hypodermic needle and a second longitudinal end opposite the first, the length of the sleeve between the first and second longitudinal ends being greater than the length of a hypodermic needle to be encased by the sheath, the tubular sleeve having a first relatively rigid tube section adjacent the first longitudinal end of the sleeve, a second relatively rigid tube section adjacent the second longitudinal end of the sleeve and an intermediate tube section joining the first and second tube sections, the intermediate tube section being made flexible by a plurality of circumferentially extending pleats to allow the first and second tube sections to be bent out of axial alignment with one another along with an encased hypodermic needle to decommission the needle within the protective sheath.

2. A protective sheath for a disposable hypodermic needle as defined in claim 1 wherein the tubular sleeve has a funnel shape at the first longitudinal end to guide a hypodermic needle into the sleeve and protect the fingers of a user.

3. A protective sheath as defined in claim 1 wherein the tubular sleeve is closed at the second longitudinal end.

4. In combination, a disposable hypodermic needle and protective sheath comprising:
    a hypodermic needle having an elongated hollow needle shaft with a puncture point at one end and a hub in which the needle shaft is mounted at the opposite end; and
    a protective sheath formed by an elongated tubular sleeve engaged with the hub of the hypodermic needle and extending in overlying relationship along the length of the elongated needle shaft beyond the puncture point, the tubular sleeve between the hub of the needle and puncture point having relatively rigid tube sections overlying the needle shaft at each end of the shaft and a flexible intermediate tube section facilitating bending and decommissioning of the hypodermic needle within the protective sheath.

5. In combination, a disposable hypodermic needle and protective sheath as defined in claim 4 wherein the hub and tubular sleeve frictionally engage one another.

6. In combination, a disposable hypodermic needle and protective sheath as defined in claim 4 wherein the hub of the needle has a lubricant spread thereon.

7. In combination, a disposable hypodermic needle and protective sheath as defined in claim 4 wherein the protective sheath has a funnel shape at one end of the elongated tubular sleeve to aid in inserting the hypodermic needle into the sheath.

8. In combination, a hypodermic needle and protective sheath as defined in claim 7 wherein the funnel shape at the one end of the sleeve is shaped and sized to extend over and beyond the hub engaged with the tubular sleeve.

9. In combination, a disposable hypodermic needle and protective sheath as defined in claim 4 wherein the intermediate tube section contains flexible tubular walls to permit the relatively rigid tube sections to be bent relative to one another.

10. In combination, the hypodermic needle and protective sheath of claim 9 wherein the flexible tubular walls of the intermediate section are formed with circumferentially extending pleats.

11. A method of decommissioning a hypodermic needle to prevent the spread of disease and contamination comprising:
    providing a protective sheath having a bendable tubular sleeve with an opening at one end of the sleeve for receiving a hypodermic needle and a sleeve length greater than the length of a hypodermic needle, the needle including a needle shaft with a puncture point at one end and a hub in which the needle shaft is mounted at the opposite end;
    inserting a hypodermic needle into the tubular sleeve through the opening at the one end of the sleeve to fully envelop the needle within the protective sheath, and then
    bending the sheath and the enveloped needle at a section of the needle shaft midway between the puncture point and the hub to capture the sheath on the needle and the needle within the sleeve.

12. A method of decommissioning a hypodermic needle as defined in claim 11 including the step of providing a funnel shape in the tubular sleeve at the opening at one end to guide a hypodermic needle into the interior passageway of the tubular sleeve.

13. A method of decommissioning a hypodermic needle as defined in claim 11 wherein the step of providing a protective sheath includes providing the tubular sleeve with relatively rigid sections at each end and a flexible section intermediate the rigid sections to facilitate bending of the sheath and the enveloped needle.

14. A method of decommissioning a hypodermic needle as defined in claim 11 wherein the step of providing the protective sheath with a flexible intermediate section includes providing a tubular sleeve with circumferentially extending pleats at the intermediate section.

15. A method of decommissioning a hypodermic needle as defined in claim 14 wherein the tubular sleeve has a funnel shape at the end with the opening for receiving the needle, and is closed at the opposite end.

16. A method of decommissioning a hypodermic needle as defined in claim 11 wherein the step of providing a protective sheath includes providing a tubular sleeve which is closed at the end opposite from the opening for receiving a hypodermic needle.

17. In combination, a disposable hypodermic needle and protective sheath comprising:

a hypodermic needle having an elongated hollow needle shaft with a puncture point at one end and a hub in which the needle shaft is mounted at the opposite end; and a protective sheath formed by an elongated tubular sleeve engaged with the hypodermic needle and extending in overlying relationship along the length of the elongated needle shaft beyond the puncture point, the tubular sleeve having relatively rigid tube sections overlying the needle shaft at each end of the shaft and a flexible intermediate tube section formed with circumferentially extending pleats to facilitate bending and decommissioning of the hypodermic needle within the protective sheath.

* * * * *